US005612057A

United States Patent [19]
Lanza et al.

[11] Patent Number: 5,612,057
[45] Date of Patent: Mar. 18, 1997

[54] ACOUSTICALLY REFLECTIVE LIPOSOMES AND METHODS TO MAKE AND USE SAME

[75] Inventors: Gregory M. Lanza, Evanston; M. Hayat Onyuksel, LaGrange; Melvin E. Klegerman, Chicago; Michael J. Vonesh, Northbrook; David L. McPherson, Chicago, all of Ill.

[73] Assignee: Northwestern University, Evanston, Ill.

[21] Appl. No.: 541,185

[22] Filed: Oct. 11, 1995

Related U.S. Application Data

[63] Continuation of Ser. No. 329,145, Oct. 12, 1994, abandoned, which is a continuation of Ser. No. 865,480, Apr. 9, 1992, abandoned.

[51] Int. Cl.$^6$ .................................................. A61K 9/127
[52] U.S. Cl. .................... 424/450; 424/1.21; 428/402.2; 436/829
[58] Field of Search ...................... 424/450; 428/402.2; 436/829

[56] References Cited

U.S. PATENT DOCUMENTS

| | | | |
|---|---|---|---|
| 4,647,447 | 3/1987 | Gries et al. | 429/2 |
| 4,857,319 | 8/1989 | Crowe | 424/94.1 |
| 4,900,540 | 2/1990 | Ryan et al. | 424/9 |
| 4,920,016 | 4/1990 | Allen | 424/450 |
| 5,116,615 | 5/1992 | Gokcen et al. | 424/94.64 |
| 5,123,414 | 6/1992 | Unger | 264/43 |
| 5,262,168 | 11/1993 | Lenk | 424/450 |

OTHER PUBLICATIONS

Szoka, et al., "Procedure for Preparation of Liposomes with Large Internal Aqueous Space and High Capture by Reverse-Evaporation", *Proc. Natl. Acad. Sci.* 75:9 4194–9418 (Sep. 1978).

Abstract, *American College of Cardiology*, No. 42644, published Feb. 26, 1992.

*Primary Examiner*—Gollamudi S. Kishore
*Attorney, Agent, or Firm*—Tilton, Fallon, Lungmus & Chestnut

[57] ABSTRACT

This invention relates to tissue specific acoustically reflective oligolamellar liposomes containing internally separated bilayers and methods to make and to use the same, alone as a perfusion ultrasonic contrast agent or conjugated to a ligand for tissue-specific ultrasonic image enhancement.

1 Claim, 9 Drawing Sheets

ACOUSTICALLY REFLECTIVE LIPOSOMES AND METHODS TO MAKE AND USE SAME

This application is a continuation of application Ser. No. 08/329,145 filed Oct. 12, 1994, abandoned which is a continuation of application Ser. No. 07/865,480 filed Apr. 9, 1992, now abandoned.

BACKGROUND OF THE INVENTION

1. Field of this invention:

This invention relates to acoustically reflective oligolamellar liposomes containing internally separated bilayers and methods to make same for ultrasonic image enhancement.

2. Description of the Prior Work in the Field:

Ultrasonic assessment of internal body organs or tissue is a well known technique. This assessment can be made by sending a signal with a waveform in the high frequency sound spectrum ($10^6$ cycles/second) and detecting the reflected ultrasound properties. In current ultrasound procedures, the inherent reflective properties of the tissue are studied.

In one recent patent, U.S. Pat. No. 4,900,540 a method for producing liposomes having an encapsulated gas is described. Liposomes are phospholipid bilayers discretely encapsulating an aqueous compartment. The composition and form of these lipid vesicles are analogous to that of cell membranes with hydrophilic polar groups directed inward and outward toward the aqueous media and hydrophobic fatty acids intercalated within the bilayer. Liposomes form spontaneously from a dry lipid film exposed to an aqueous medium and may be unilamellar and/or multilamellar. Unilamellar vesicles are typically classified as small (20 to 200 nm diameter) or large (approximately 1 micron). Multilamellar liposomes are classically described as having concentric bilayers, an "onion morphology". A type of multilamellar liposome termed oligolamellar liposomes are typically described as multilamellar liposomes with increased aqueous space between bilayers or have liposomes nested within bilayers in a nonconcentric fashion. Liposomes have many uses but are considered to be highly desirable for drug delivery and diagnostic applications.

As previously discussed, the "540" patent discloses a method for producing liposomes having an encapsulated gas. It is said that these liposomes can be injected for in vivo enhancement of organ imaging with ultrasound. A gas charged particle in vivo, however, may not be stable. Thus, it is desirable to develop a stable acoustically reflective liposome by controlling composition, structure and size alone.

SUMMARY OF THE INVENTION

This invention provides acoustically reflective liposomes amenable to ligand conjugation for targeted ultrasonic enhancement. These liposomes enhance the acoustic, reflectivity based solely on their composition, structure and size. This invention provides an acoustically reflective oligolamellar liposome containing internally separated lipid bilayers. More specifically, this invention provides an acoustically reflective liposome particle made by incorporating phosphatidylethanolamine with other lipids and having a mean particle size of between about 0.8 and 10 microns. This composition has a oligolamellar structure and it is theorized that the resultant lamellar structure together with the mechanical properties of the phospholipid bilayer make the liposomes acoustically reflective. The liposomes typically include phospholipids such as phosphatidylcholine and phosphatidylethanolamine and can also include cholesterol.

This invention further provides a composition wherein the acoustically reflective liposome may be conjugated to a tissue specific ligand. Preferably, this ligand is an antibody or antibody fragment.

The acoustically reflective liposome of this invention can be made by incorporating phosphatidylethanolamine into a typical phosphatidylcholine based liposome particle, reducing the size of the particle to less than about 400 nm, lyophilizing the particle, and reducing the particle size to between about 0.8 and 10 microns. This liposome particle can be chemically altered to covalently couple a tissue specific ligand. As an alternative to lyophilization, the acoustically reflective liposomes of this invention can be made by double-emulsion method in an organic solvent such as triolein or by repeated freeze-thawing of the liposomes. This invention further provides a method to prepare targeted, acoustically reflective liposomes to characterize specific tissues involving administering ligand-conjugated acoustically reflective, oligolamellar liposomes containing internally separated bilayers devoid of gas, and measuring ultrasonic reflectance of the specific tissue of interest before and after liposome administration and comparing the results for enhanced acoustic reflectance. Specifically, this method can be used to characterize a ventricular thrombus; although many other types of tissue can be analyzed. This invention also provides a method to enhance tissue perfusion (i.e. use as a contrast agent). In these situations, the contrast agent could be the liposome without conjugated ligands.

This invention also provides a method to monitor a drug delivered in a liposome administered to a patient's circulatory system. This method involves mixing a liposome containing the drug targeted to specific tissue and (if the drug containing liposome is not acoustically reflective) an acoustically reflective liposome devoid of any gas targeted to the same tissue to form a dispersion, administering the dispersion to a patient and monitoring the delivery of the liposome containing the drug by detecting the acoustically reflective liposome.

DETAILED DESCRIPTION OF THE INVENTION AND BEST MODE

In accordance with this invention, acoustically reflective liposomes are provided which may be used alone as an ultrasonic contrast agent or which are conducive to site specific ligand conjugation to enhance ultrasonic imaging of specific tissues types or receptors in the body.

The inventors have discovered that the echogenicity of liposomes is a function of composition, morphology and size. With respect to morphology, the inventors have found that liposomes may be simply produced by mechanical dispersion of a dried phospholipid film (e.g. phosphatidylcholine) into an aqueous medium. This procedure typically produces classical multilamellar and fewer oligolamellar vesicles. The addition of phosphatidylethanolamine imparts morphological changes to the arrangement of the bilayers. It is hypothesized that the head groups of the phosphatidylethanolamine results in this acoustically reflective arrangement, speculated to be an oligolamellar type of liposome. Furthermore, liposomes with similar acoustic properties may be produced by the inclusion of charged lipids, (e.g. phosphatidylserine) which could lead to a more oligolamellar distribution secondary to internal repulsion of the lipid bilayers.

More specifically, the above described oligolamellar liposomes possess a series of membrane-fluid interfaces that in the aggregate are ultrasonically reflective. Liposomes produced by the same method, but without the incorporation of phosphatidylethanolamine or charged lipids (e.g. pure phosphatidylcholine vesicles) are not echogenic, despite their multilamellar morphology, because the bilayers are typically closely opposed and act as a single acoustic interface.

Figure 1:
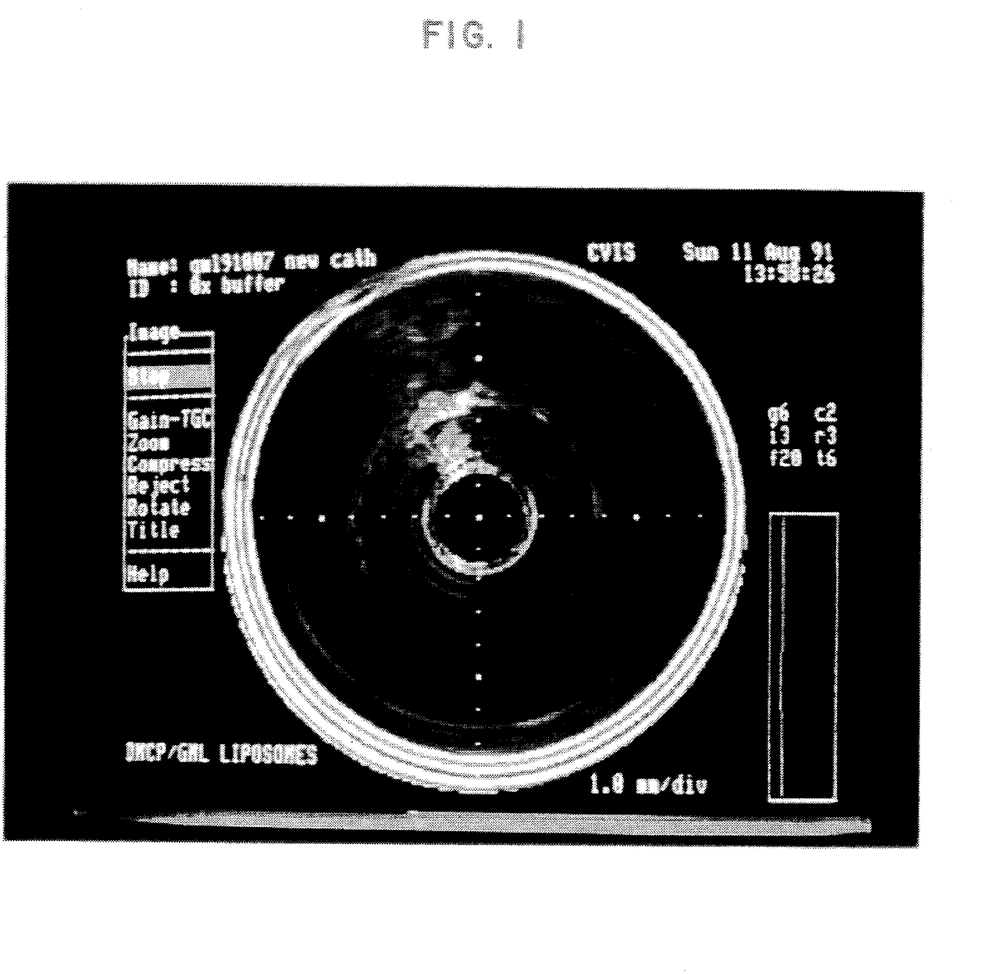
FIG. 1 is an ultrasonic image of a buffer control obtained in vitro using 20 MHz intravascular catheter.
Figure 2:
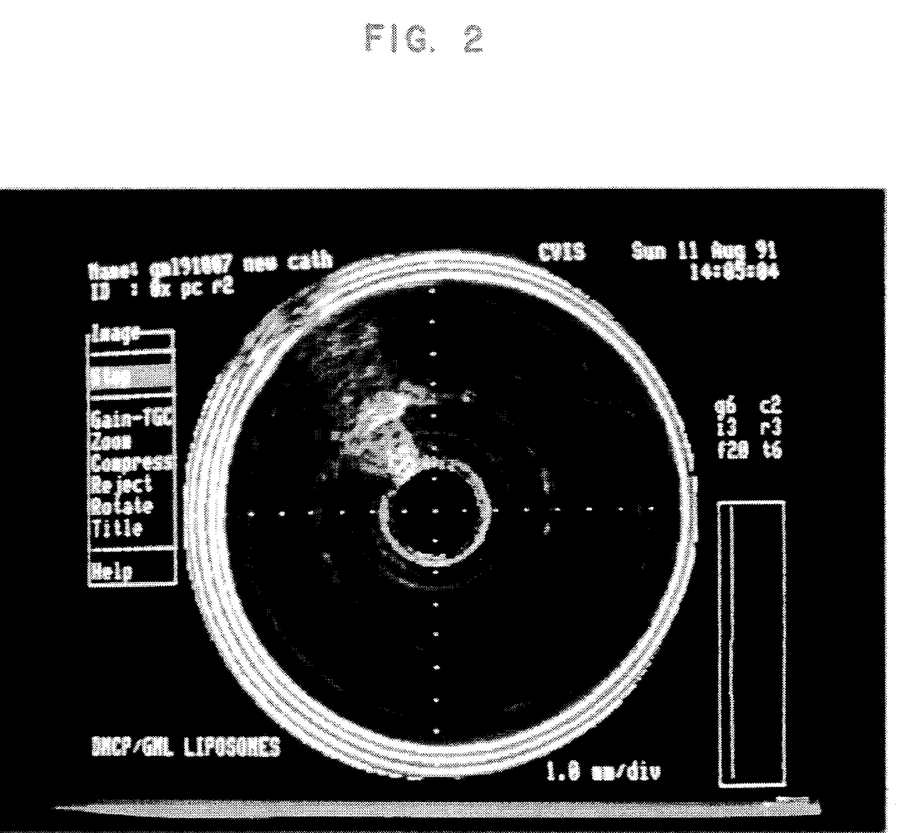
FIG. 2 is an ultrasonic image of pure phosphatidylcholine vesicles prior to extrusion through NUCLEPORE (Costar Co.) membranes obtained in vitro using 20 MHz intravascular catheter.
Figure 3:
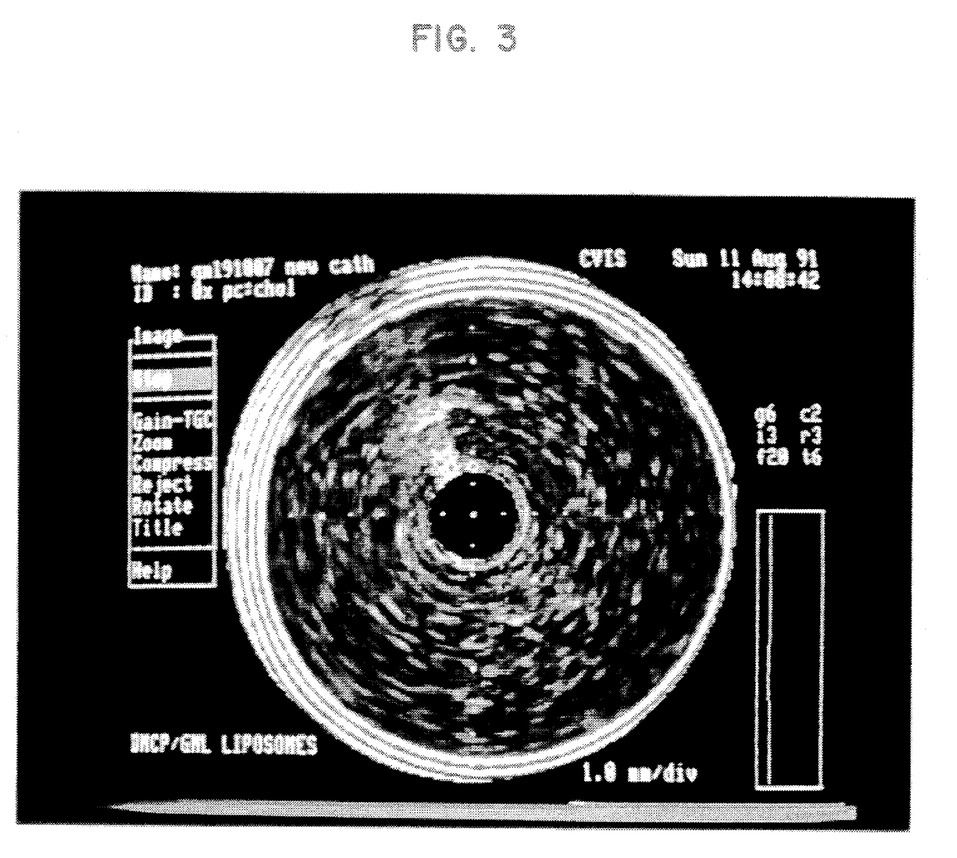
FIG. 3 is an ultrasonic image of phosphatidylcholine and cholesterol vesicles prior to extrusion obtained in vitro using 20 MHz intravascular catheter.
Figure 4:
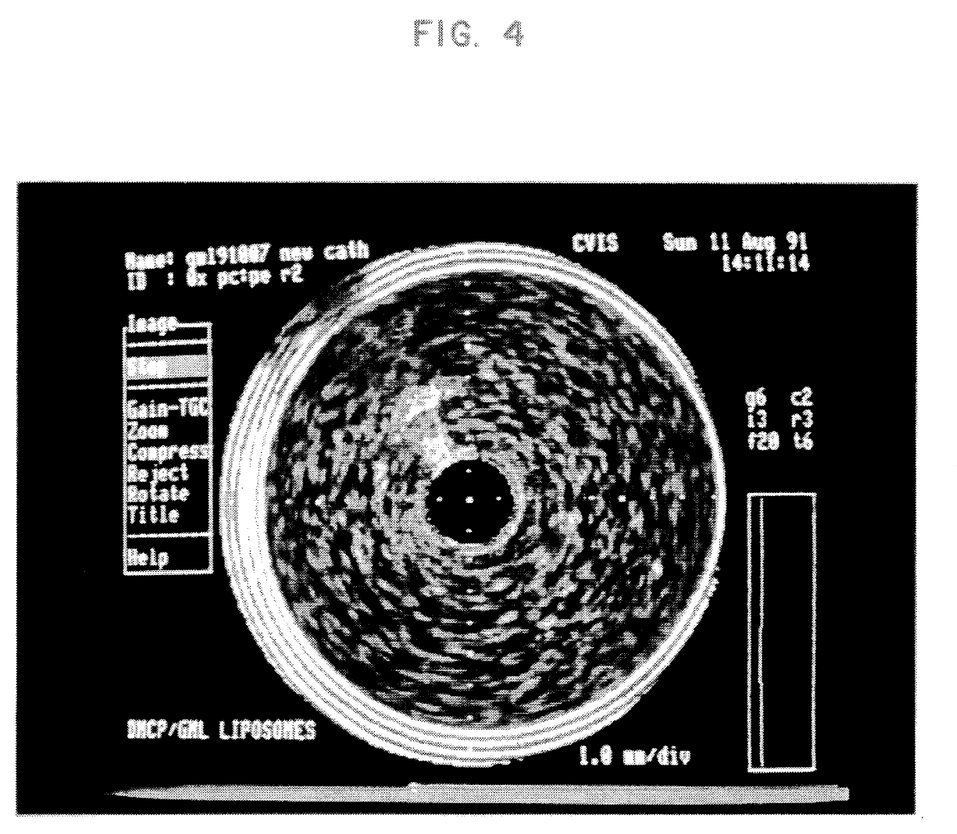
FIG. 4 is an ultrasonic image of phosphatidylcholine and phosphatidylethanolamine vesicles prior to extrusion in vitro using 20 MHz intravascular catheter.
Figure 5:
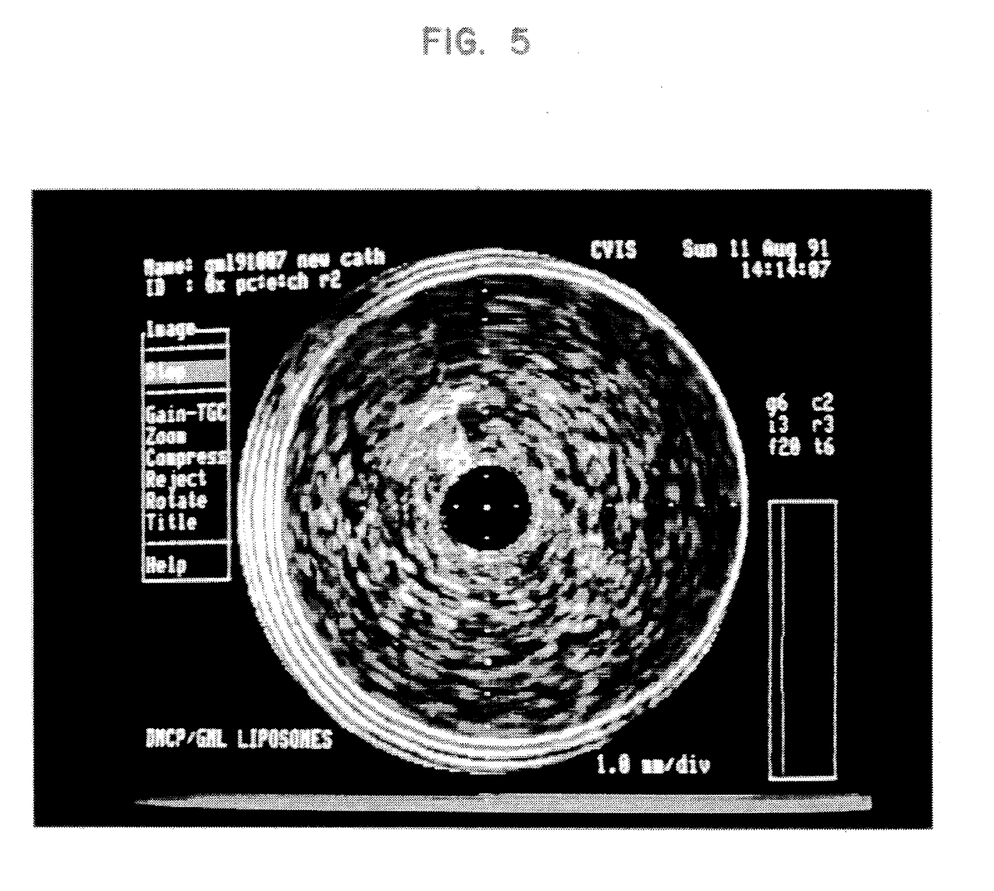
FIG. 5 is an ultrasonic image of phosphatidylcholine, phosphatidylethanolamine and cholesterol vesicles prior to extrusion in vitro using 20 MHz intravascular catheter.
Figure 6:
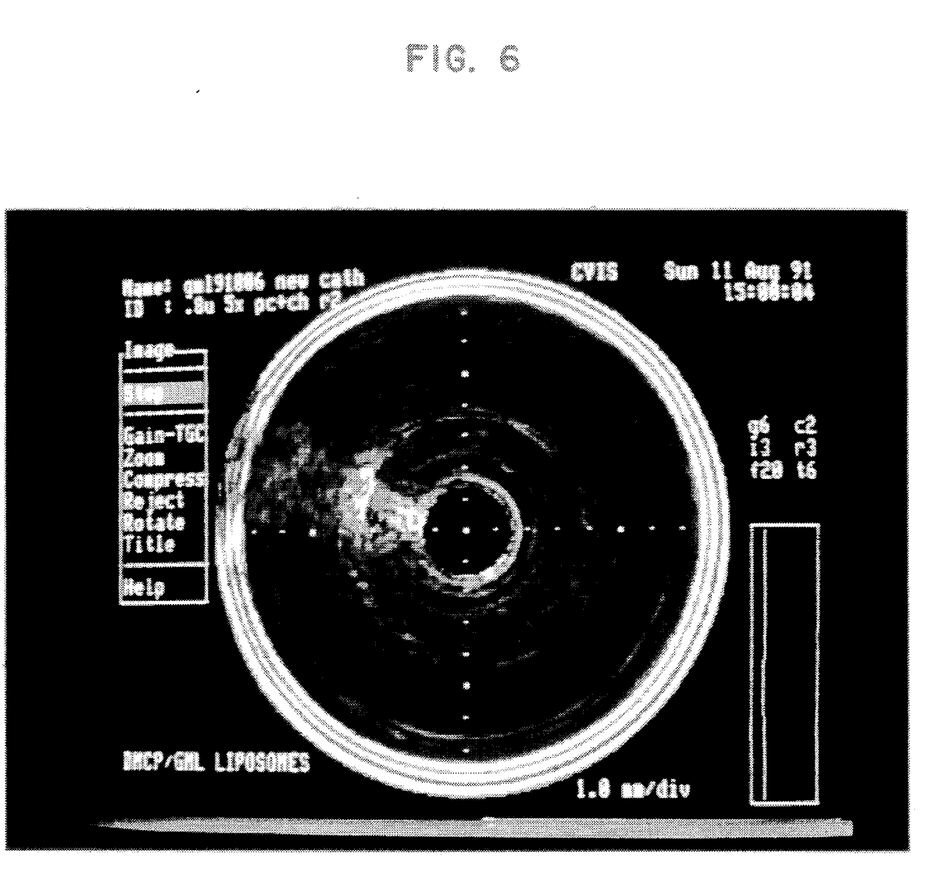
FIG. 6 is an ultrasonic image of a phosphatidylcholine and cholesterol vesicles after extrusion in vitro using 20 MHz intravascular catheter.
Figure 7:
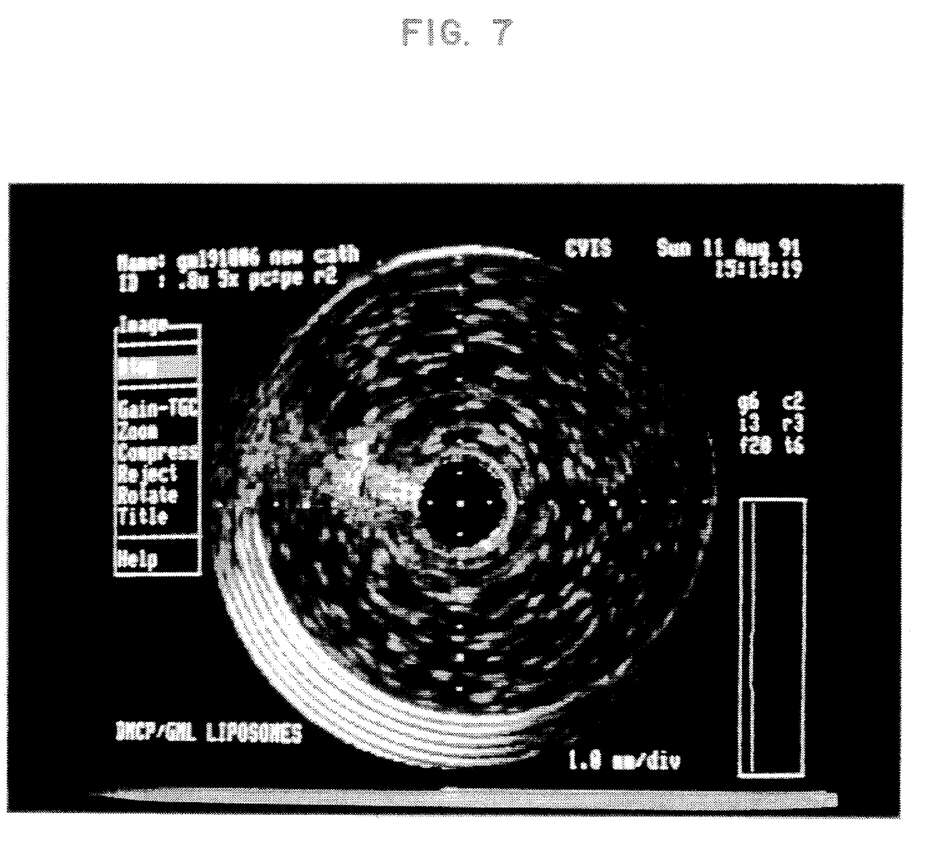
FIG. 7 is an ultrasonic image of phosphatidylcholine and phosphatidylethanolamine vesicles after extrusion obtained in vitro using 20 MHz intravascular catheter.
Figure 8:
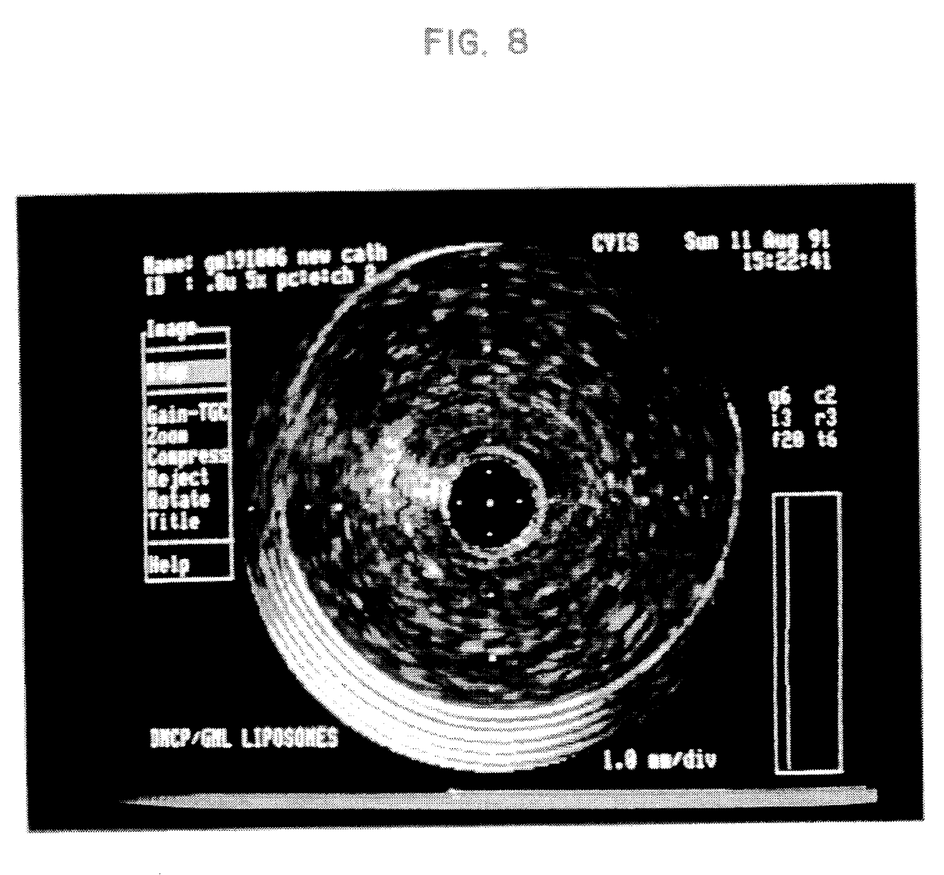
FIG. 8 is an ultrasonic image of phosphatidylcholine, phosphatidylethanolamine and cholesterol vesicles after extrusion obtained in vitro using 20 MHz intravascular catheter.
Figures 9A, 9B:
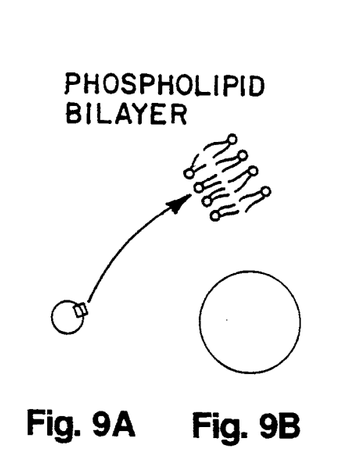
FIGS. 9A–E are schematic drawings of different types of liposome particles.
Figure 9C:
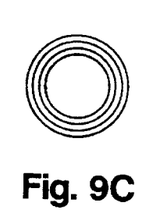
Figure 9D:
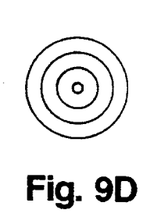
Figure 9E:
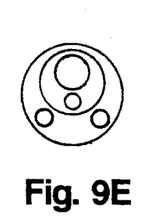

Although both classic multilamellar and oligolamellar liposomes may be created directly from a dried lipid film without lyophilization, the inventors suspect that the classical multilamellar form predominates this approach and that such vesicles are less echogenic than the oligolamellar form which may predominate after rehydration of freeze-dried liposomes. See FIG. 9. FIG. 9A demonstrates a small unilamellar liposome, FIG. 9B a large unilamellar liposome, FIG. 9C a classical multilamellar liposome (classical), FIG. 9D and 9E two types of oligolamellar liposomes (concentric and vesicular respectively) Liposomes 9A, 9B and 9C are nonechogenic, i.e. minimally acoustically reflective. It is believed that liposomes 9A, 9B and 9C do not have a sufficient number of interfaces for detectable acoustic reflection. Liposomes 9D and 9E are echogenic, i.e. acoustically reflective probably due to the bilayers being separate enough to give sufficient reflective interfaces.

Ultrasonically reflective liposomes may be created by any procedure which creates oligolamellar vesicles with internally separated bilayers. The inventors have demonstrated the use of liposome composition (i.e. phosphatidylethanolamine incorporation) to create this effect, but one can easily envision mechanical means to the same end. One example is the conjugation of ligands (i.e. antibodies, peptides, lectins, etc,) to lipid components of the membrane then incorporation of these components between layers of the multilamellar vesicles by a suitable process. In this scenario, the relatively large size of the ligands bound to the inner and outer bilayer surfaces could either primarily spread or secondarily enhance the separation of multilamellar bilayers.

Oligolamellar liposomes may be prepared by but are not limited to the following processes: lyophilization, repeated freeze-thaw, a modified double emulsion technique. Production through lyophilization is the current standard operating procedure. The acoustically reflective liposome particle is made by combining phosphatidylethanolamine with other lipids (e.g. phosphatidylcholine) into a dried film, resuspending the film with deionized water with or without cryoprotectant, to form a liposome, reducing the size of the particles to less than about 400 nm, lyophilizing the particles, and resuspending the particles in buffer. Particles may then be extruded to a size between about 0.8 and 10 microns. This method is the most conducive to conjugating protein ligands since it avoids exposure of the protein to organic solvents, evaporation or mechanical destruction. The antibody is conjugated in an aqueous buffer to unilamellar liposomes less than 400 nm in diameter for maximum efficiency and the conjugate may be freeze-dried with mannitol to help protect the peptide while allowing the vesicles to structurally degrade.

Alternatively, in the modified double emulsion method, an organic solution containing triolein, phospholipids and cholesterol is combined on a volume to volume basis with an aqueous solution typically containing materials to be entrapped. This solution is vigorously agitated to form a water-in-oil emulsion. This emulsion is then combined with a sucrose solution and agitated again, creating a water-in-oil-in-water emulsion, or a double emulsion. Evaporation of the organic solvent leaves multicompartmental liposomes. This method is compatible with liposome encapsulation of but is less conducive for conjugate with proteins or other biological macromolecules (Kim, S., Turker, M. S., Chi, E. Y., Sela, S. and Martin, G. M., 1983 Biochim. Biophys. Acta 728,339; Gao, K. and Huang, L., 1987 Biochim. Biophys. Acta 897, 377).

Another method for producing oligolamellar liposomes is a variant of the lyophilization method and involves freezing and thawing of small unilamellar liposomes (Pick, U. 1981 Arch. Biochem. Biophys., 212, 186). The repeated freeze-thawing of liposomes leads to membrane rupture and reannealing into larger multicompartmental vesicles. These membranes typically incorporate charged phospholipids into the bilayers to provide a nidus for ice crystal formation. Although the protein ligands could easily be conjugated to the smaller unilamellar liposomes, repeated freeze-thawing of biologically active proteins may destroy their bioactivity and reduce their efficacy as targeting ligands.

The liposomes which have been found to be useful in this invention incorporate phosphatidylethanolamine into the bilayer liposomes that can be formed into a vesicular structure. The liposome can be formed from lipids such as phosphatidylcholine (PC) and phosphatidylethanolamine (PE). Preferably the phosphatidylcholine ranges from about 50 to 95 mol % of the lipid content of the liposome, but can generally range from 60 to 90 mol % of the liposome, while phosphatidylethanolamine preferably ranges from 2 to 20 mol %, but generally from about 5 to 10 mol percent of the lipid content of the liposome.

Incorporation of cholesterol, another neutral lipid, has been found to contribute an echogenic component to liposomes which was lost after polycarbonate extrusion, suggesting that large liposome size increases echogenicity.

Work by Rhoden and Golden (Rhoden, V and Goldin, S 1979 Biochemistry 18, 4173) has indicated that incorporating cholesterol into the lipid bilayer will increase particle size while, the addition of charged phospholipids decrease vesicle size. Cholesterol intercalates within the phosphatidylcholine bilayer with very little change in area by occupying the regions created by the bulky phosphatidylcholine headgroups. This increases the packing density and structural stability of the bilayer and may contribute to acoustic character (New, R. R. C., 1990 In New, R. R. C. (ed): Liposomes: a practical approach, (ed), Oxford University Press, New York, pp 19–21).

With respect to size, it was found that liposomes of approximately one to four microns in size were lyophilized without excipients and were echogenic upon resuspension with Tris buffer, pH 7.5. Additionally, it was found that decrease of prelyophilization particle size to less than one micron with probe sonication and a sugar excipient resulted in echogenic liposomes. During lyophilization, the smaller vesicles may break down more completely and enhance the lipid interactions upon rehydration. The addition of sugar (mannitol) was selected to provide bulk to the lyophilized powder without cryoprotecting the vesicle size. Other sugars, such as trehalose or maltose can be used to provide bulk, but also tend to preserve liposome integrity during freeze-drying and may be contraindicated in the production of echogenic liposomes from small unilamellar liposomes.

The smaller the liposomes the higher the ultrasonic frequency required to resolve the vesicle. In practice, a single liposome (1–2 microns) is not resolvable with commercially available diagnostic ultrasonic transducers. However, discrete liposomes and the coalescence of liposomes either randomly in solution or secondary to specific targeting ligands contribute to ultrasonic scattering, and can create an acoustic interface which may be visualized and quantified. Moreover, in vivo, targeted echogenic liposomes will benefit from enhanced echogenicity secondary to creation of multiple liposome-tissue interfaces and a transient increase in target tissue size and density.

An acoustically reflective liposome particle generally ranges from 0.8 to 10 microns, but preferably 1.0 to 2.0 microns.

In summary, the lyophilization method (refered to as dehydration-rehydration procedure) appears to provide the preferred method for creating echogenic, protein-targeted liposomes. The small unilamellar vesicles are optimum for protein conjugation and can be ruptured and enlarged into multivesicular liposomes without destroying the biological activity of the ligand. This method was first suggested by Kirby and Gregoriadis (Kirby, C. and Gregoriadis, G., 1984 Biotechnology 2, 979 (hereby incorporated by reference) for the purpose of increasing liposome entrapment efficiency. The inventors have discovered that liposomes produced by this method with the appropriate chemical composition are echogenic and suitable for targeting.

The acoustically reflective liposomes can be conjugated to a site specific ligand such as an antibody, lectin, peptide or nucleic acid. A variety of methods have been reported to attach proteins to liposomes covalently. (Martin, F. J., Heath, T. D. and New, R. R. C., 1990 In Liposomes: a practical approach. Oxford University Press, New York, pp 163–182; hereby incorporated by reference). The most popular methods involve synthesis of thiol-reactive lipids using either N-succinimidyl-pyridyl-dithioproprionate (SPDP) or N-succinimidyl-(4-[p-maleimidophenyl])-butyrate (SMPB). SPDP produces a reversible disulfhide bond and SMPB produces an irreversible thioester. The conjugation process is essentially the same for both reagents and the inventors have elected to use SPDP for in vitro experiments reported herein.

S-acetylmercaptosuccinic anhydride can be used instead of SPDP with a substitution of hydroxylamine for dithiothreitol in the process to reduce the number of purification steps required (Martin, F. J., et al. Supra. 163–182).

Another method described by Heath et al. (Heath, T. D., Maher, B. A. and Paphadjopoulos, D., 1981: Biochim. Biophys. Acta 599, 42) involves the use of periodate to create a Schiff base between glycolipids incorporated into the lipid membrane and primary or secondary amino groups on proteins. This method provides 20% binding of the initial protein with a theoretical maximum of 40%. Conjugation to larger liposomes appears better than smaller unilamellar liposomes, a factor which may be less desirable for producing echogenic liposomes by lyophilization.

Phosphatidylethanolamine can also be derivatized by attaching a bifunctional straight-chain (6–8 carbons) dicarboxylic acid which can bridge between the lipid and protein. The phosphatidylethanolamine may be derivatized by either a di-N-hydroxysuccinimide derivative or by reaction with carbodiimide. The former route must be used with a process which prepares liposomes rapidly without significant subsequent processing. The carbodiimide method is prone to extensive cross-linking and often requires citraconylate blocking of endogenous amino groups. This blocking reagent is removed at pH 4.4 which may precipitate peptides or begin to hydrolyze the liposome membranes (Martin, F. J., et al. Supra. at 163–182).

Liposomes can be conjugated with Protein A or Protein G, which have inherent affinity for immunoglobulins. Liposomes can be conjugated with avidin, which strongly binds to biotin that can be attached to immunoglobulins or other ligands thereby effecting of the coupling a ligand to liposomes. Finally, sugars and other oligosaccharides may be conjugated to liposomes containing a pure or SPDP-derivatized phosphatidylethanolamine via endogenous aldehyde groups of the saccharide by introducing a thiol residue onto the sugar or by carboxylating free hydroxyl groups with succinic anhydride followed by a carbodiimide coupling reaction (Martin, F. J., et al. Supra at 163–182).

An acoustically reflective liposome particle may be used alone as an ultrasonic contrast agent or with a ligand conjugation for specifically targeted ultrasonic image enhancement. More specifically, ligand-targeted, acoustically reflective liposomes may be used to enhance ultrasonic imaging of intravascular structures as well as extravascular structures accessible due to increased permeability of the vasculature or by direct administration into a nonvascular space. The potential cardiovascular targets include myocardial tissue (antimyosin antibody), vascular clot (anti-fibrin antibody), vegetations (anti-bacterial determinant antibody), endothelial surface (anti-receptor or surface determinant antibody) and tumors (anti-tumor antibody). Additionally, other tissue structures in the penetrable spaces of joints, (lymphatic system; vrogenital or pulmonary bronchial alveolar tree) may be ultrasonically enhanced with specific acoustically reflective liposomes administered directly into these spaces.

The routes of administration include intravascularly, intralymphatically, intrathecally, intraurologically, intracapsularly, and bronchial lavage. The acoustically reflective liposome made be administered as a bolus of liposomes or as an infusion in a pharmaceutically acceptable carrier such as saline or glucose in water.

As with other injected pharmaceutical agents, the acoustically reflective liposome, is administered as a sterile compound. To prepare a sterile composition of matter the acoustically reflective liposome is prepared under aseptic conditions using sterilized buffers and reagents.

Visualization of the in situ liposomes is possible with virtually all ultrasonic imaging modalities, including intravascular (catheter-based), transcutaneous transvascular/epicardial (conventional echocardiography, vascular or high frequency) and transesophageal echocardiography. The precise imaging technique appropriate for a given application must take into account the clinical objective of the procedure, anatomic site of interest and medical condition of the patient.

Two important uses for liposome enhancement to tissue would be the following. First, the standard transcutaneous or transesophageal ultrasound would be used to identify cardiac structure. Liposomes would subsequently be used to enhance structure definition, either through their perfusion into a vascular bed to identify regions of perfusion (i.e. myocardial) or to identify pathologic structures by directly or indirectly "highlighting" of the target. The transducers that are used utilize probes from 2 to 15 MHz and are placed transcutaneously/transvascular/epicardially/or transesophageally to image cardiovascular structures.

In the second instance, liposomes would be utilized in conjunction with intravascular ultrasound imaging devices. These devices generate images of vascular structure and operate at a frequency of 10–100 MHz. These catheters do not generally impede blood flow and they would be directed to the region of interest with the liposomes highlighting structures such as plaque, thrombus or endothelial receptors/determinants.

Using either the intravascular or the transcutaneous/transvascular/epicardial/transesophageal method, the 2-dimensional B-mode ultrasound images generated are amenable to more sophisticated image processing and/or analysis. Grayscale texture analysis, radiofrequency signature analysis and a variety of additional complementary ultrasonic material characterization techniques may find use in enhancing the interpretation of these data.

EXAMPLE 1

Production of Echogenic Liposomes Using a Lyophilization Methodology "Best Mode"

This procedure describes methods and reagents required to make acoustically reflective, oligolamellar liposomes using a composition and method conducive to the production of antibody targeted vesicles. Freeze-drying is lyophilization Reagents:
1) Phosphatidylcholine, from egg yolk (PC) as an alcoholic solution
2) Cholesterol (Chol)
3) Phosphatidylethanolamine, dipalmitoyl (PE)
4) Deionized water
5) Cryoprotectant sugar (e.g. mannitol)
6) Tris HCl
7) Sodium Phosphate (dibasic)
8) Sodium Chloride Equipment:
1) Rotary evaporator with external cooling, vacuum and heating.
2) Probe sonicator and ear protection.
3) Submicron particle size analyzer (e.g. NICOMP (Pacific Scientific) Malvern) and tubes.
4) Volumetric flasks, graduated cylinders, syringes, hypodermic needles, repipets/pipets and liquid scintillation vials (25 & 10 mL).
5) Stirrer/heating plate and stir bars.
6) Electronic balance (accurate to 0.1 or 0.01 mg).
7) pH meter and calibration standards.
8) Ring stand and clamps.
9) NUCLEPORE (Costar Co.) filters and membranes in steps from 2 to 0.22 microns.
10) Bottle lyophilizer and associated equipment.
11) CVIS intravascular catheter system and 20 MHz imaging catheter.

Procedure:
1) Warm vials of phosphatidylcholine to room temperature.
2) Weigh (according to electronic scale instructions) 25 mg of cholesterol.
3) Dissolve cholesterol in 2.5 mL of dry chloroform and phosphatidylethanolamine in 2.0 ml of dry chloroform using sufficient warming to facilitate dissolution but avoiding excess heat.
4) Combine in a 250 mL rotoevaporator flask: 73 mg of phosphatidylcholine, 11 mg phosphatidylethanolamine and 16 mg of cholesterol. Adjust as required for scale-up.
5) Attach flask to pre-cooled (0 degrees Centigrade) rotary evaporator with a 50 degree Centigrade warming bath.
6) Rotate flask rapidly (approximately 210 rpm) and dry under vacuum.
7) After the film is dry, remove flask from rotoevaporator and place in desiccator under vacuum and cover desiccator with a dark cloth.
8) Continue to dry film under vacuum for 2 days.
9) Prepare 100 mM mannitol solution in deionized water.
10) Add 10 mL of mannitol solution per 100 mg of lipid.
11) Without significant agitation, place flask on rotoevaporator without coolant circulating, flood atmosphere with nitrogen and rotate the flask (approximately 210 rpm) to resuspend lipid film.
12) When lipid film is resuspended, add one or two drops of liposome suspension to NICOMP (Pacific Scientific) tube and dilute with 100 mM mannitol solution, sufficiently for analysis.
13) Analyze particle size with NICOMP (Pacific Scientific) according to manufacturer's instructions.
14) Transfer liposomes from round bottomed flask to 25 mL liquid scintillation vial with a pipet and cap.
15) Secure vial to ring stand and submerge vial approximately two-thirds into a cool tap-water bath to dissipate excess heat during sonication.
16) Remove cap and position sonicator probe into the vial being sure not to leave the probe in contact with the glass and maintaining the tip of the probe about one quarter inch above the bottom.
17) Set the sonicator for 10% duty and 10% power and sonicate for 3 minutes.
18) Recheck particle size as before with NICOMP (Pacific Scientific). Continue to reduce particle size using 1 minute sonication bursts at same power and with increasing duty levels until vesicles are less than 400 mn. Increase power and repeat duty changes starting at 10% if additional sonication is required.
19) Transfer approximately 5 mL aliquots of liposome suspension into each of two 25 mL liquid scintillation vials, layer with nitrogen, and cap.
20) Either snap-freeze in acetone-alcohol-dry ice bath or freeze overnight in −70 Centigrade deep freezer.

21) Transfer vials from the freezer to the lyophilizer jars and freeze dry according to manufacturer's instructions for approximately 48 hours.
22) After 48 hours of lyophilization, remove vials from the freeze dryer, gently overlay contents with nitrogen, recap and seal vials with parafilm.
23) Store vials in refrigerator with desiccant up to 72 hours until use.
24) Prepare 0.10M Tris HCl+0.10M NaCl, pH 7.5 buffer.
25) To rehydrate, add 0.10 mM Tris HCl+0.10 mM NaCl, pH 7.5, buffer to each vial. A good starting volume is 2–3 mL of buffer/mL of the desired liposome lyophilized.
26) Size liposomes with the NICOMP (Pacific Scientific) submicron particle analyzer as previously discussed.
27) Transfer liposome suspension to an appropriately sized syringe and extrude liposomes to desired particle size through polycarbonate membranes according to manufacturer's instructions until desired size is attained. Excessive extrusion will significantly destroy liposome structure and diminish echogenicity. If initial particle size is more than 1–2 microns above desired range, repeat procedure using a greater post-lyophilization dilution factor to attain a smaller initial vesicle size. Be sure sample for size analysis dilution buffer is iso-osmotic with liposome solution (300 milliosmoles) to avoid artifactual swelling or contraction of vesicles and inaccurate size estimation.
28) Transfer liposomes into small (10 mL) liquid scintillation vials and image liposome suspension with 20 MHz cm CVIS intravascular imaging catheter system.

Reference: New, R. R., 1990, Liposomes: A Practical Approach. Oxford University Press. (hereby incorporated by reference).

EXAMPLE 2

A. SPDP Derivitization of Phosphatidylethanolamine

The following procedures described methods to produce an N-succinimidyl pyridyl dithiopropionate (SPDP) derivitization of IgG antibody and phosphatidylethanolamine and their incorporation into a process for producing acoustically reflective liposomes as described in Example 1. This procedure describes methods and reagents required to make N-succinimidyl pyridyl dithiopropionate derivatives of phosphatidylethanolamine for incorporation into liposomes for antibody coupling reaction.

Reagents:
1) L-a-phosphatidylethanolamine, dimyristoyl or dipalmitoyl, 99% purity (PE)
2) Triethylamine (TEA)
3) N-sucinimidyl pyridyl dithiopropionate
4) Nitrogen
5) Silicic Acid
6) Methanol
7) Chloroform
8) Dodecamolybdophosphoric acid
9) Silica thin layer chromatography (TLC) plates Equipment:
1) Liquid scintillation vial or test tube with cap
2) Stirrer/heating plate and stir bars
3) 20 cc plastic syringe barrel with glass fiber plug
4) Fraction collector or test tube rack
5) TLC developing tank with filter paper lining
6) Electronic balance (accurate to 0.1 or 0.01 mg)
7) Graduated cylinders, repipets/pipets
8) Ring stand and clamps
9) Atomizer sprayer and spray box
10) Rotary evaporator with external cooling, vacuum, heating and 250 mL flasks.
11) Hamilton microliter syringe with lock Procedure:
1) Weigh 15 mg of PE, 10 mg of SPDP, 2 g silicic acid, 3 g dodecamolybdophosphoric acid.
2) Dissolve PE in a liquid scintillation vial in approximately 2 mL chloroform using sufficient warming to facilitate dissolution but avoiding excess heat.
3) Dry PE under continuous nitrogen stream or with rotoevaporation.
4) Resuspend PE in 2.0 mL of chloroform.
5) Dissolve 200 microliters TEA in 25 mL methanol (2.9 mg/0.5 mL).
6) Dissolve 10 mg SPDP in 0.5 mL methanol with slight supplemental heating.
7) Add 0.5 mL TEA (2.9 mg) to PE in vial.
8) Add 0.5 mL SPDP (10 mg) to PE and TEA.
9) Add small stirring bar to vial.
10) Saturate atmosphere in vial with nitrogen and cap.
11) Stir mixture at room temperature for 2 hours.
12) In a 250 mL or greater flask add 130 mL of chloroform, 50 ml of methanol, and 10 ml of deionized water.
13) If solution is cloudy add 1–2 mL additional methanol to dry.
14) Add approximately half of the solution to the developing tank.
15) Cover tank and allow atmosphere and filter paper lining to saturate with solvents.
16) Slurry 2 g of silicic acid in 10–12 mL of chloroform.
17) Pour silicic acid slurry into syringe barrel supported on a ring stand.
18) Allow excess solvent to drain but do not allow column to dry.
19) Prepare phosphomolybdate spray by dissolving 3 g of dodecamolybdophosphoric acid in 10 mL of ethanol or reagent grade alcohol.
20) Place in sprayer and wrap sprayer in foil to blockout light until use.
21) After 2 hours check reaction by spotting (10 microliters) the reaction mixture and pure phosphatidylethanolamine standards with a Hamilton syringe onto the thin layer chromatography plate.
22) When the solvent line on TLC plate is approximately 1.0 cm from the top, remove the plate from the tank and air dry.
23) In a hood, spray dry plate with a light, even coat of phosphomolybdate spray.
24) Warm plate on a hot plate with low heat to develop black spots (100 degrees Centigrade). The test is qualitative. Derivatized phosphatidylethanolamine migrates faster than the pure standard lipid. The reaction is usually 100% complete. If the reaction is incomplete, add 1 mg of TEA and allow reaction to continue 30–60 minutes and recheck with thin layer chromatography.
25) When the reaction is complete, add mixture to silicic acid column and wash in with 4.0 mL chloroform.
26) Elute derivatized phosphatidylethanolamine in 2.0 mL fractions using 4.0 mL aliquots of the following chloroform:methanol solutions gradient: 4.0:0.25, 4.0:0.50 4.0:0.75, 4.0:1.0, 4.0:1.25, 4.0:1.5, 4.0:1.75, 4.0:2.0. Repeat 4.0:2.0 to ensure complete elution.
27) Layer each fraction with nitrogen after collection to inhibit oxidation.
28) Identify fractions with phosphatidylethanolamine derivative by thin layer chromatography as before.

29) Pool fractions containing derivative into a rotoevaporator flask.
30) Attach flask to rotoevaporator previously cooled with circulating cold water or coolant.
31) Dry derivative to a film and resuspend in 3.0 cc of chloroform.
32) With thin layer chromatography roughly quantitate phosphatidylethanolamine derivative concentration by comparing 15 μL, 10 μL, and 5 μL spots of standard PE of known concentration to equal volumes of the derivative solution. Determine mg/mL of derivative.

B. N-succinimidyl Pyridyl Dithiopropionate Derivitization of IgG Antibody

This procedure describes the N-succinimidyl pyridyl dithiopropionate derivitization of IgG antibody for conjugation with similarly modified liposomes.

Reagents:
1) N-succinimidyl pyridyl dithiopropionate (SPDP)
2) Sodium citrate
3) Anhydrous sodium phosphate, dibasic
4) Sodium chloride
5) Sephadex G-50
6) Ethanol or reagent grade alcohol
7) IgG antibody
8) BCA protein binding dye concentrate (BCA)
9) Dithiothreitol
10) Deionized water
11) Sodium acetate
12) Nitrogen
13) Dilute hydrochloric acid (HCl)
14) Glacial acetic acid (17.4M)
15) Anhydrous potassium phosphate, monobasic Equipment:
1) UV/VIS Spectrophotometer
2) 100 mL Gel Chromatography column and tubing
3) Fraction collector
4) Micropipets
5) Hamilton syringe (5–10 μL capacity)
6) Pasteur pipets
7) Beaker/flasks various sizes
8) Stirrer and stir bars
9) Analytical balance (accurate to 0.1 or 0.01 mg)
10) pH meter with micro and regular electrodes and appropriate standards
11) Ring stand and clamps
12) Amicon ultrafiltration system
13) Volumetric flasks Procedure:
1) Combine 19.7 g sodium citrate, 7.1 g anhydrous sodium phosphate, dibasic ($Na_2HOP_4$), and 2.9 g sodium chloride per liter in a 1 or 2 liter beaker and fill 75% with highly purified, deionized water. Usually prepare 2 L of buffer.
2) Adjust pH to 7.0 using dilute hydrochloric acid.
3) Transfer pH 7.0 buffer to volumetric flask with three washes of the beaker and fill to the mark with deionized water.
4) Weight 7.5g of SEPHADEX G-50 (Pharmacial Co.) and transfer to a 125 mL beaker.
5) Add 100 mL of citrate/phosphate buffer (step 1) to the beaker, cover and allow gel to swell at least 3 hours, preferably overnight.
6) After swelling, decant excess citrate/phosphate buffer and fines and resuspend gel in 100 mL of fresh buffer.
7) Assemble gel chromatography system.
8) Place 10 mL of citrate/phosphate buffer in base of column.
9) Load gel slurry into column as a continuous pour while draining excess buffer out of the column.
10) After column is poured, allow gel to settle.
11) Pass 10 bed volumes (approximately 750 mL) of citrate/phosphate buffer through the column and seal for use the next day. (Add 0.01% sodium azide to elution buffer if storing the column for more than 24 hrs).
12) The next day, drain excess buffer from the top of the column, leaving 5 mL above gel.
13) Prepare 0.1M phosphate buffer, pH 7.5, by mixing 1.361 g anhydrous potassium phosphate, monobasic ($KH_2PO_4$), in 90 mL of deionized water, titrate to pH 7.5, transfer to a 100 mL volumetric flask and fill to the mark with deionized water.
14) Prepare 0.5M acetic acid by diluting 2.0 mL of concentrated acetic acid (17.4M) with 67.6 mL deionized water.
15) Prepare 6 mg N-succinimidyl pyridyl dithiopropionate in 1.0 mL 30% ethanol.
16) Weigh 165 mg sodium acetate, combine with 10 mL deionized water and titrate to pH 5.5.
17) Weigh 95 mg dithiothreitol and dissolve in 250 microliters of sodium acetate buffer in a microcentrifuge tube.
18) Dissolve IgG antibody (e.g. 25 mg) in 0.1M phosphate buffer (pH 7.5) at a concentration of 5 mg/mL.
19) Add 150 microliters of N-succinimidyl pyridiopropionate in 30% ethanol while stirring slowly, and continue stirring for 30 minutes.
20) Slowly decrease the pH (dropwise) of the antibody solution to pH 5.5 with 0.5M acetic acid.
21) Add 50 microliters of dithiothreitol, cover solution with nitrogen and allow to stand 1 hour.
22) Drop the buffer level over SEPHADEX (Pharmacia) column to top of column and slowly add IgG mixture.
23) Run IgG into column and wash in with 2–3 mL citrate/phosphate buffer.
24) Fill column to top with buffer previously purged of oxygen with nitrogen, careful not to disturb column, and attach buffer reservoir layered with nitrogen or argon or continuously bubble nitrogen through the elution buffer.
25) Elute column at 0.5 to 1.0 mL/min.
26) Layer each fraction with nitrogen or argon to avoid oxidation of sulfhydryl groups.
27) Assay fraction on spectrophotometer at 280 nm and note protein peaks. Usually, two peaks are detected but the first protein peak is used. The second peak is probably immunoglobulin fragments, though no confirmatory electrophoresis has been performed.
28) Combine fractions of high optical density and conduct a BCA protein assay according to manufacturer's instructions to estimate protein concentration.
29) If the protein concentration is too dilute, to concentrate antibody under nitrogen or argon with Amicon ultrafiltration system according to the manufacturer's instructions.
30) Combine antibody with liposomes as previously discussed and proceed with conjugation.

C. Production of Echogenic Antibody-conjugated Liposomes Using a Freeze-drying Methodology This procedure describes methods and reagents required to make acoustically reflective, oligovesicular liposomes conjugated to IgG antibodies through a disulfide bridge using N-succinimidyl pyridyl dithiopropionate derivatives of phosphatidylethanolamine and antibody.

Reagents:
1) SPDP derivatized L-a-phosphatidylethanolamine (PE-PDP)

2) Phosphatidylcholine (PC)
3) Cholesterol (Chol)
4) Phosphotidylglycerol (PG)
5) Deionized water
6) Mannitol
7) Sodium citrate
8) Sodium phosphate (dibasic)
9) Sodium chloride
10) Reagent grade alcohol
11) Biogel A-5M (100–200 Mesh)

Equipment:
1) Rotary evaporator with external cooling, vacuum and heating
2) Probe sonicator and ear protection
3) Submicron particle size analyzer (e.g. Malvern, Coulter) and tubes
4) Fraction collector or test tube rack
5) Volumetric flasks
6) Stirrer/heating plate and stir bars
7) Electronic balance (accurate to 0.1 or 0.01 mg)
8) Liquid scintillation vial or suitable substitute
9) Graduated cylinders 10) Repipets/pipets
11) Ring stand and clamps
12) NUCLEPORE (Costar Co.) filters and membranes from 2 to 0.22 microns Procedure:
1) Warm vials of phospatidylcholine to room temperature.
2) Weigh 25 mg of cholesterol.
3) Dissolve cholesterol in 2.5 mL of chloroform.
4) Transfer to a rotoevaporator by pipet 73 mg of phospatidylcholine, 11 mg derivatized phospatidylethanolamine, 16 mg cholesterol. Adjust as required for scale-up.
5) Attach flask to 0 degree centigrade pre-cooled rotoevaporator with 50 degree centigrade warming bath.
6) Dry lipid film under vacuum at rotational speed of approximately 210 rpm.
7) Remove flask from rotary evaporator and place in desiccator under vacuum and cover desiccator with a dark cloth.
8) Dry film for 2 days.
9) Prepare 100 mM mannitol solution in deionized water.
10) Add 10 mL of mannitol solution per 100 mg of lipid.
11) Rotate the flask at 210 rpm to resuspend lipid film.
12) When lipid film is resuspended, add one to two drops to NICOMP tube and dilute with 100 mM sugar water solution.
13) Analyze particle size.
14) Transfer liposomes from round bottomed flask to liquid scintillation vial.
15) Secure vial to ring stand and submerge vial approximately two-thirds into cool tap water flask to dissipate excess heat during sonication.
16) Position sonicator probe about one quarter inch above the flask bottom and not in contact with the glass vial.
17) Set the sonicator for 10% duty and 10% power and sonicate for 3 minutes.
18) Recheck particle size. Continue to reduce particle size using 1 minute sonication bursts at same power and with increasing duty levels until vesicles are less than 400 nm. Increase power and repeat duty changes starting at 10% if additional sonication is required.
19) Derivatize antibody as previously described.
20) To conjugate reduced antibody to liposomes, combine liposomes with reduced, derivatized protein to have a coupling ratio (µg protein/µmol lipid—0.6 mg protein/µmol lipid) of 390–500 and a final protein concentration of approximately 0.5 mg/mL. Buffer associated with protein should provide sufficient buffering capacity to maintain pH at 7.0 at a minimal ionic strength.
21) Allow antibody conjugation to proceed for 12–18 hours.
22) Fill chromatography column with gel at a ratio of at least 10 mL of BIOGEL-A 5M (100–200 mesh) to 1 mL of liposome suspension. Put 10 mL of buffer in column before adding gel and then fill the column while slowly running out the excess buffer.
23) Elute Biogel-A-5m column with 10 bed volumes of 100 mM mannitol solution the day before use.
24) After antibody conjugation, pass liposomes through sequentially smaller (2 to 0.22 micron) NUCLEPORE (Costar Co.) polycarbonate filters as required to reduce particle size below 400 nm. Verify final particle size.
25) Drain excess buffer from column.
26) Gently and slowly load liposome suspension to top of column with a Pasteur pipet.
27) Slowly run liposomes into column, stopping the flow when the liposomes have just completely entered the top of the column. Do not allow the column to dry.
28) Wash liposomes off the sides of column with 2–3 mL of mannitol solution then run this into the column.
29) Slowly fill the column with 100mM mannitol solution containing 0.01M potassium phosphate buffer, pH 7.0 being careful not to disturb the top of the gel column.
30) When the column is full of buffer, attach the buffer reservoir to the column with tubing.
31) Attach column to fraction collector with sufficient tubes to collect 3 bed volumes. Liposomes will come out in the void volume and unbound antibody will follow close behind.
32) Collect fractions at a rate of 0.5–1.0 mL/min for best resolution.
33) Analyze fractions for particles using the NICOMP at maximum photopulse to isolate liposomes and a spectrophotometer at 280 nm to isolate protein fractions.
34) Pool fractions containing both liposomes and protein.
35) Concentrate liposomes to approximately 10 mg of lipid per mL using an appropriately sized Amicon ultrafiltration system (300 KDa membranes) according to the manufacturer's instructions.
36) Transfer 5 mL aliquots of liposomes into 25 mL liquid scintillation vials, layer with nitrogen and cap.
37) Either snap-freeze in acetone-alcohol-dry ice bath or freeze overnight in −70 degree centigrade deep freezer.
38) Transfer vials from the freezer to the lyophilizer jars and freeze dry for 48 hours according to the manufacturer's instructions.
39) After 48 hours of lyophilization, remove vials from the freeze dryer, gently layer contents with nitrogen, recap and seal with parafilm.
40) Store vials in refrigerator with desiccant until use within 72 hours.
41) Prepare 0.10M Tris HCl+0.10M NaCl, pH 7.5, buffer.
42) To rehydrate, add 0.10 mM Tris HCl+0.10 mM NaCl, pH 7.5, buffer to each vial. The initial liposome size will vary inversely with the volume of buffer added. A good starting volume is 2–3 mL of buffer/mL lyophilized liposome containing sufficient amount of ions to make a solution of the same osmolarity/mL of liposome suspension lyophilized.
43) Size liposomes with submicron particle analyzer.
44) Transfer liposome suspension to an appropriately sized syringe and extrude liposomes to desired particle size through polycarbonate membranes according to manufacturer's instruction until desired size is attained. Note: Excessive extrusion will significantly destroy liposome structure and diminish echogenicity. Be sure sample dilution buffer size analysis is iso-osmotic with liposome solution to avoid artifactual swelling or contraction of vesicles and inaccurate size estimation.

45) Transfer liposomes into small 10 mL liquid scintillation vials and image liposome suspension with 20 MHz CVIS intravascular imaging catheter system.

EXAMPLE 3

Liposomes of four different compositions were prepared in triplicate using the procedures outlined in Example 1 (without the optional addition of mannitol cryopotectant) and imaged with a 20 MHz intravascular catheter to identify echogenicity. Two replicates were ultrasonically analyzed pre and post extrusion and the results of an overall split-plot statistical analysis y=rep+composition+rep* composition+ time+composition*time+residual, where rep*composition was used to test composition effects and residual error was used to test time effects (time equating to pre versus post polycarbonate extrusion). FIGS. 1 through 8 are examples from the second replicate pre and post polycarbonate extrusion. Least-square means for the composition effect for the above model are presented.

| Composition | Liposome Mean Gray Scale | Liposome Gray Scale Heterogeneity |
| --- | --- | --- |
| PC | 3.31 | 3.34 |
| PC:CH | 9.82 | 8.33 |
| PC:PE | 21.68* | 11.94* |
| PC:PE:CH | 23.85* | 13.86* |

*PC vs other combination ($p \leq 0.05$)

In this study, change in solution acoustic reflectivity was quantitated as the increased pixel brightness (gray scale) of liposome clusters compared with background levels and the increase in pixel heterogeneity of the overall liposome/buffer image. Liposomes incorporating phosphatidylethanolamine were ultrasonically visible before and after extrusion to reduced particle sizes and this was reflected as a statistically significant increase in pixel gray scale and heterogeneity. Phosphatidylcholine: cholesterol vesicles were echogenic before but not after extrusion.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. An acoustically reflective oligolamellar liposome for use in ultrasonic imaging consisting essentially of phosphatidylethanolamine and an additional lipid selected from the group consisting of phosphatidylserine, cholesterol, phosphatidylglycerol and phosphatidylcholine, wherein said liposome has a particle size of 0.8 to 10 microns and has internally separated bilayers and a ligand selected from the group consisting of an antibody, a peptide, a lectin and a nucleic acid is conjugated to said bilayers to increase the separation of the bilayers and the echogenicity of said liposome.

* * * * *

UNITED STATES PATENT AND TRADEMARK OFFICE
CERTIFICATE OF CORRECTION

PATENT NO : 5,612,057
DATED : March 18, 1997
INVENTOR(S) : Lanza et al.

It is certified that error appears in the above-identified patent and that said Letters Patent is hereby corrected as shown below:

Title Page: item [73] Assignee, after "Evanston, Ill.," add the following: -- and Board of Trustees University of Illinois, Chicago, IL --

Signed and Sealed this

Thirteenth Day of March, 2001

Attest:

NICHOLAS P. GODICI

Attesting Officer

Acting Director of the United States Patent and Trademark Office